(12) United States Patent
Altshuler et al.

(10) Patent No.: US 8,348,933 B2
(45) Date of Patent: Jan. 8, 2013

(54) METHOD AND APPARATUS FOR PROCESSING HARD MATERIAL

(75) Inventors: Gregory B. Altshuler, Lincoln, MA (US); Andrei V. Belikov, St. Petersburg (RU)

(73) Assignee: Laser Abrasive Technologies, LLC, Walpole, MA (US)

( * ) Notice: Subject to any disclaimer, the term of this patent is extended or adjusted under 35 U.S.C. 154(b) by 789 days.

(21) Appl. No.: 11/767,496

(22) Filed: Jun. 23, 2007

(65) Prior Publication Data
US 2008/0003536 A1 Jan. 3, 2008

Related U.S. Application Data

(63) Continuation of application No. 10/410,578, filed on Apr. 9, 2003, now Pat. No. 7,267,672.

(60) Provisional application No. 60/371,097, filed on Apr. 9, 2002.

(51) Int. Cl.
*A61B 18/20* (2006.01)
*A61C 1/00* (2006.01)
(52) U.S. Cl. .................. 606/13; 606/3; 606/10; 433/29
(58) Field of Classification Search .............. 607/88–93; 606/3, 10, 11, 13, 14, 16–18; 433/29–31
See application file for complete search history.

(56) References Cited

U.S. PATENT DOCUMENTS

| | | | |
|---|---|---|---|
| 4,503,853 A | 3/1985 | Ota et al. | |
| 5,020,995 A | 6/1991 | Levy | |
| 5,060,527 A | 10/1991 | Burgess | |
| 5,199,870 A | 4/1993 | Steiner et al. | |
| 5,257,935 A | 11/1993 | Vassiliadis et al. | |
| 5,257,956 A | 11/1993 | Ewen | |
| 5,267,856 A | 12/1993 | Wolbarsht et al. | |
| 5,328,365 A | 7/1994 | Jacoby | |
| 5,334,016 A | 8/1994 | Goldsmith et al. | |
| 5,401,171 A | 3/1995 | Paghdiwala | |
| 5,409,376 A | 4/1995 | Murphy | |
| 5,456,603 A | 10/1995 | Kowalyk et al. | |
| 5,458,594 A * | 10/1995 | Mueller et al. | 606/3 |
| 5,554,029 A * | 9/1996 | Kowalyk et al. | 433/215 |
| 5,636,983 A | 6/1997 | Shoji et al. | |

(Continued)

FOREIGN PATENT DOCUMENTS

DE 4211233 A1 8/1993

(Continued)

OTHER PUBLICATIONS

Altshuler, G. B., "Human tooth in low and high intensive light fields," Proc. SPIE vol. 2623, 1996, pp. 68-87.

(Continued)

*Primary Examiner* — Ahmed Farah
(74) *Attorney, Agent, or Firm* — Patentbar International, P.C.

(57) ABSTRACT

A method and apparatus are provided for processing a hard material, for example a hard biological material such as dental enamel or bone, with optical radiation. A treatment zone of the material is selectively cleaned of ablation products and other dirt to enhance processing efficiency, and a tip through which the optical radiation is applied to the treatment zone of the hard material is spaced slightly from the treatment zone during at least a portion of the time that hydrating fluid is being applied to the zone and/or while air or another gas is applied to the zone to clean the surface thereof.

11 Claims, 8 Drawing Sheets

U.S. PATENT DOCUMENTS

| | | | |
|---|---|---|---|
| 5,734,765 A | 3/1998 | Artjushenko et al. | |
| 5,746,596 A | 5/1998 | Gallant et al. | |
| 5,752,948 A | 5/1998 | Tankovich et al. | |
| 5,785,521 A | 7/1998 | Rizoiu et al. | |
| 5,785,703 A | 7/1998 | Goodman et al. | |
| 5,800,165 A | 9/1998 | Kirsch et al. | |
| 5,873,875 A | 2/1999 | Altshuler | |
| 5,957,691 A | 9/1999 | Goodman et al. | |
| 5,968,035 A | 10/1999 | Goodman et al. | |
| 6,083,218 A | 7/2000 | Chou | |
| 6,135,774 A | 10/2000 | Hack et al. | |
| 6,137,110 A | 10/2000 | Pellin et al. | |
| 6,155,824 A | 12/2000 | Kamen et al. | |
| 6,162,055 A | 12/2000 | Montgomery et al. | |
| 6,270,342 B1 * | 8/2001 | Neuberger et al. | 433/29 |
| 6,331,111 B1 | 12/2001 | Cao | |
| 6,497,572 B2 | 12/2002 | Hood et al. | |
| 6,558,372 B1 | 5/2003 | Altshuler | |
| 6,723,090 B2 | 4/2004 | Altshuler et al. | |
| 7,048,731 B2 | 5/2006 | Altshuler | |
| 7,288,086 B1 * | 10/2007 | Andriasyan | 606/14 |

FOREIGN PATENT DOCUMENTS

| | | |
|---|---|---|
| DE | 19520787 A1 | 1/1996 |
| DE | 19533348 A1 | 5/1996 |
| SU | 1593669 A | 9/1990 |
| WO | 00-62694 A1 | 10/2000 |
| WO | 02-17811 A1 | 3/2002 |

OTHER PUBLICATIONS

Finkelstein, L. H. et al., "Epilation of Hair-Bearing Urethral Grafts Using the Neodymium:YAG Surgical Laser," The Journal of Urology, vol. 146, 1991, pp. 840-842.

Goldman, L. et al., "Laser Treatment of Tattoos," JAMA, Sep. 11, 1967, vol. 201, No. 11, pp. 163-166.

Morgan, J. et al., "GRP78 Induction by Calcium Ionophore Potentiates Photodynamic Therapy Using the Mitochondrial Targeting Dye Victoria Blue BO," Photochemistry and Photobiology, 1998, vol. 67, No. 1, pp. 155-164.

Wolbarsht, M. L, ed., "Laser Applications in Medicine and Biology," vol. 1, Plenum Press, New York, 1971, pp. 1-63.

International Search Report, mailed Aug. 27, 2003, from related International Application No. PCT/US03/10768, filed Apr. 9, 2003.

* cited by examiner

METHOD AND APPARATUS FOR PROCESSING HARD MATERIAL

CROSS REFERENCE TO A RELATED APPLICATION

This application claims the benefit of an earlier filing date of a co-pending U.S. patent application Ser. No. 10/410,578, filed on Apr. 9, 2003.

FIELD OF THE INVENTION

This invention relates to the processing of hard material, and, more particularly, to the processing of such hard material with optical radiation.

BACKGROUND OF THE INVENTION

Hard material such as a metal, dental material, such as filling material or dental prosthesis material, or a hard bio-tissue, for example tooth enamel dentine or bone, has heretofore been ablated or otherwise processed by directing optical radiation, and in particular, laser radiation, at the material. However, the inventors have found that such procedures have in the past been less optimally efficient for a number of reasons.

In particular, where a laser, for example an Er laser, is being used to ablate bio-tissue such as tooth enamel, the efficiency of the ablation can be significantly enhanced by assuring adequate water content on the surface of the material being treated and by keeping the irradiated surface of the material free of dirt. The first condition is important because water collected in natural cavities and in micro-cracks produced in the material due to laser treatment may expand as a result of irradiation, thereby assisting in the ablation process, and can also generate shock waves which also facilitate the process. The second condition is important to prevent dirt, including particles of ablation, from interfering with light flow to the tissue surface, such interference resulting both from such dirt blocking radiation from reaching target material and from absorbtion of radiation by such dirt. It has been found by the inventors that the second condition alone can increase ablation efficiency by roughly 30% to 100%. The two conditions together can result in a many-fold increase in efficiency.

However, hydrating and cleaning the tissue or other hard material during treatment is normally difficult where the light guide through which the radiation is applied to the material is in contact with the material, as is preferably the case, the light guide preventing water from reaching the tissue under the light guide for hydration, and preventing ablation products from leaving the area under the light guide. Except for embodiments such as that shown in application Ser. No. 09/549,406, or other embodiments where ablation products and other energy resulting from the ablation process are recycled, contact between the light guide and/or any particle or other energy reflector rounding the light guide and the tissue during irradiation is usually desirable in that it results in less photon loss, and thus higher ablation efficiency. By hydrating, cleaning and recycling energy lost from the ablation process, optimum enhancement of ablation efficiency can be achieved, permitting smaller and less expensive radiation sources to be used for the material processing.

A need therefore exists for a method and apparatus which facilitates hydration and cleaning of hard material, and in particular hard tissue such as tooth enamel, during ablation/processing of the material, and which preferably also facilitates recycling of ablation products/lost energy, so as to optimize ablation/processing efficiency. Improved and novel laser sources which take advantage of the lower energy requirements resulting from the enhanced ablation efficiency to provide required energy with smaller and less expensive units are also desirable.

SUMMARY OF THE INVENTION

In accordance with the above, this invention provides a method and apparatus for processing a hard material with optical radiation from a suitable source. The radiation is applied through a tip to a surface in a treatment zone of the material, and the treatment zone is cleaned by a suitable mechanism of dirt, including products of ablation. The tip is slightly spaced from the material surface during at least most of the time a gas, such as air, is applied by a suitable mechanism to the surface for the cleaning thereof. A hydrating fluid such as water may also be applied by a suitable mechanism to the treatment zone, the tip through which radiation is applied being slightly spaced from the surface of the material during at least a portion of the time the hydrating fluid is being applied. the thickness of a water layer formed by the hydrating fluid on the treatment surface is limited to prevent radiation energy loss. The radiation may be applied as a sequence of pulses at a selected repetition rate, with the gas being applied during intervals between at least selected ones of the radiation pulses. the hydrating fluid may also be applied at least in part between at least selected ones of the radiation pulses. The applying of the hydrating fluid may be followed by the applying of the gas between the same radiation pulses, the hydrating fluid and the gas may be applied during different intervals between pulses or the applying of hydrating fluid may overlap with at least selected ones of the radiation pulses.

For some embodiments, the tip is in contact with the surface of the material during irradiation of the surface and the tip is selectively raised a slight distance from the surface by a suitable mechanism during the application of at least one of the hydrating fluid and the gas, and preferably both. the mechanism for selectively raising the tip may be driven hydraulically, pneumatically, mechanically, electrically, magnetically or by using energy of ablation. The hydrating fluid and/or the gas may be applied under pressure, with the fluid/gas pressure being used to raise the tip. The tip may also be scanned by a suitable mechanism in a direction substantially parallel to the treatment surface, which mechanism may include a feedback mechanism to facilitate control of the scan for enhanced cleaning.

The radiation source may be a laser diode pumped solid state laser. The radiation source may be wholly located within the apparatus or the solid state laser may be located in the apparatus and be connected to a diode pumping array by at least one optical fiber. In the later case, each diode of the array may be connected to the solid state laser in a side pumping geometry. The source may also have the geometry of a monolithic or flexible fiber laser, or may be a diode laser or a pumped laser cooled by phase change material. the residual of any phase change material used to cool the source may be used to cool the treatment zone. The solid state laser and the pumping diodes may also be mounted as an array in heat sinking electrodes which are cooled by a pressurized gas, the array being mounted in the apparatus.

Particles of ablation and other energy from the ablation may be returned to the treatment surface to enhance the efficiency of the ablation by a reflector or other suitable mechanism.

The hard material being processed may be hard biological tissue, for example bone or hard dental tissue such as enamel, or may be dental material such as filling material or material used for various dental prosthesis.

The forgoing objects features and advantages of the invention will be apparent from the following more detailed description of the invention as illustrated in the accompanying drawings, common elements in the various figures having the same or comparable reference numerals.

DETAILED DESCRIPTION OF THE INVENTION

In general, the invention involves selectively providing hydration, cleaning and/or recycling of energy resulting from ablation to enhance ablation efficiency and providing a small gap between the tip of an optical light guide used to direct radiation to the material surface, at least during periods when hydration of the surface being treated is occurring and during cleaning of the surface. For some embodiments, the gap may also be provided during irradiation to facilitate the recycling of ablation products/energy to the material. For other embodiments, the tip is in contact with the treated surface during irradiation and recycling may be primarily of energy. The improved efficiency of the ablation permits the process to be performed using smaller and less expensive laser radiation sources, and in particular diode laser or diode/fiber laser pumped radiation sources which may be small enough to fit in a treatment hand-piece.

Figure 8:
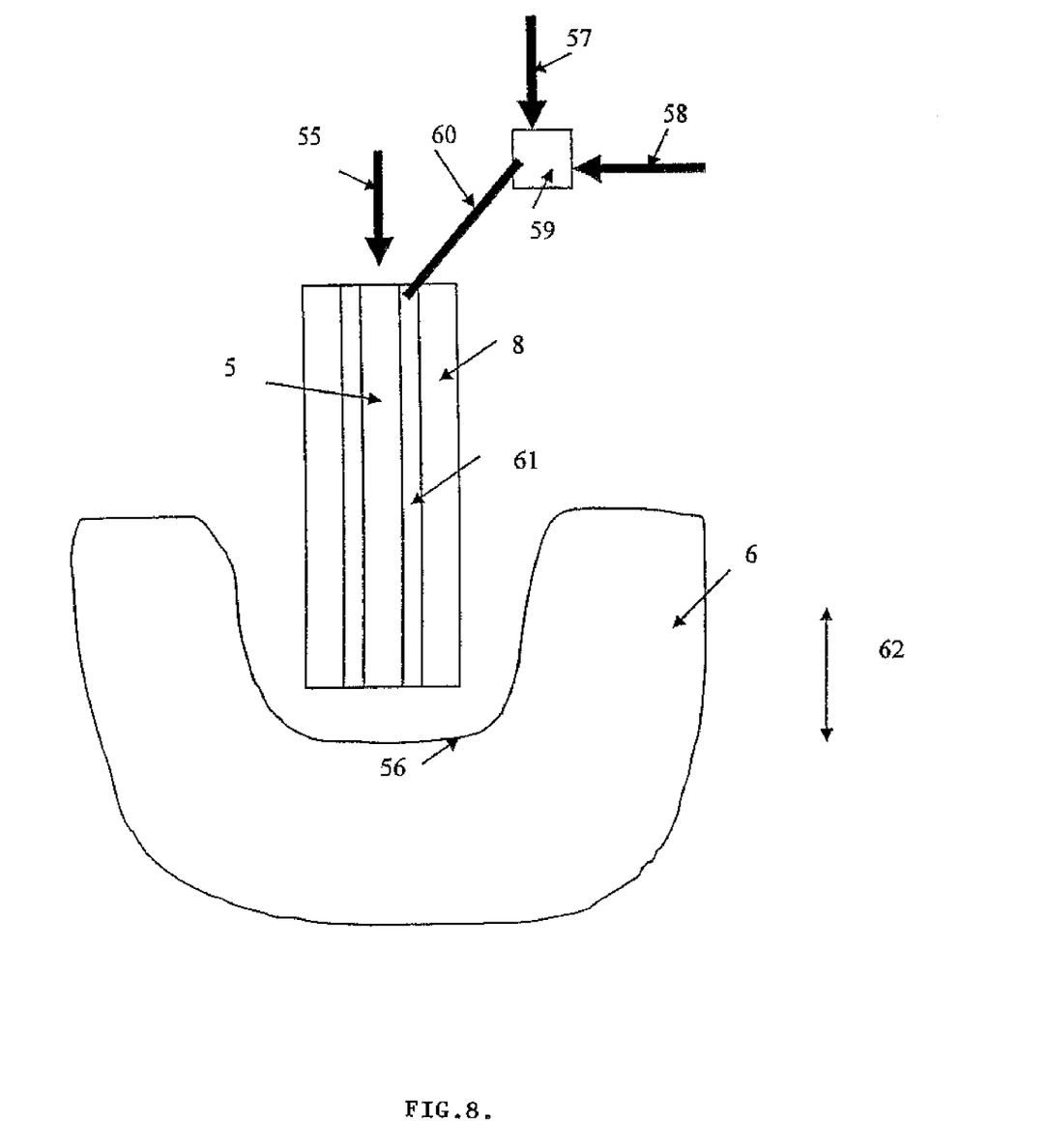
FIG. 8 is a schematic representation illustrating the novel concepts of this invention.

FIG. 8 illustrates the general concept of the novel method and apparatus of this invention. Light pulse 55 passes through optical tip 5 and is delivered to processed zone 56 of the tissue or material 58. Gas 57 and liquid 58 flow through controlling valve 59, channel 60 and gap 61 between tip 5 and surrounding tube 8 to the same zone 56. The gas pulses are selectively synchronized with the light pulse. Pressure pulses formed as a result of the gas pulse increase the gap between of treated zone 60 and the end of the tip between light pulses, thereby cleaning residual products of ablation produced as a result of the light pulses. Water or other liquid pulses may be delivered to the treatment zone between gas pulses for hydration, cooling and/or initiation of the ablation process. The tip is thus oscillating in direction 62 as a result of the above actions.

Figure 1:
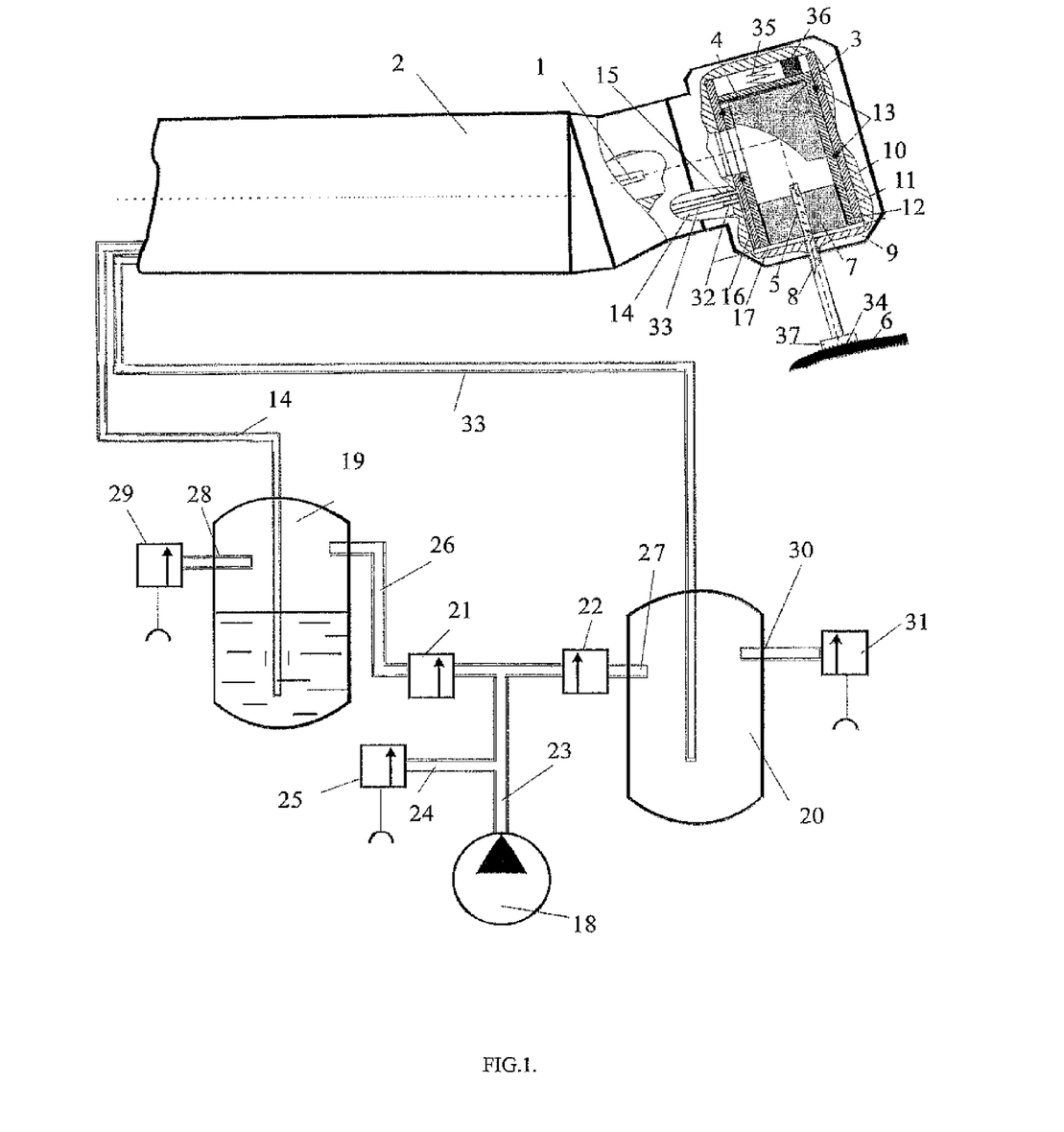
FIG. 1 is a partially cut-away illustration of one embodiment of apparatus in accordance with the invention.

FIG. 1 is a semi-schematic, partially cut-away view of a first embodiment for practicing the teachings of the invention. For this embodiment, laser radiation from a source (not shown), for example a laser rod, is applied through an optical fiber or other suitable optical component 1 fixed in a handle or other housing 2 to an optical reflector 3 mounted in a housing 4. Optical radiation reflected from reflector 3 is directed through an optical guide or tip to the object being treated, for example hard tooth tissue. Optical tip 5 is fixed at its light-receiving end in a holder 7 and extends through an optically opaque tube 8 mounted in a housing 10 and in a cover 9 for the housing. Tube 8 may be of any suitable material, but, if not a disposable component, is preferably of a material harder then the material being treated, for example stainless steel, ceramic or tungsten. Housing 10 is attached to handle 2. A fixed sleeve or tube 11 is mounted inside housing 10 and a movable/traveling sleeve or tube 12 is mounted inside tube 11. Holder 7 is hermetically attached to movable tube 12, for example by threading. Tubes 11 and 12 have adjacent indentations in which sealing rings 13 are mounted. Cover 9, housing 10, and tubes 11, 12 have aligned openings formed therein through which radiation from fiber 1 passes.

Pressurized water is applied from tank 19 through tube 14, coupling 15, and channel 16 to space 17. Tube 14 extends into the water in tank 19. Pressurized air is applied from tank 20 through connecting tube 33, coupling 32 and a channel (not shown) which extends to space 17 between housing 10 and tube 11 at a location radially spaced from channel 16. Compressor 18 pressurizes both tanks 19 and 20 through tube 23 and valve 21/tube 26 and valve 22/tube 27 respectively. Compressor 18 is also connected to atmosphere through tubes 23, 24 and valve 25. Valve 25 is normally closed. Tank 19 is incompletely filled with water and can connect to atmosphere through tube 28 and normally closed valve 29. Tank 20 connects to atmosphere through tube 30 and normally closed valve 31.

To provide water to space 17, compressor 18 is turned on, valve 22 is closed, valve 21 is opened, and valves 25 and 29 are closed. Water flows from space 17 to the space between optical tip 5 and tube 8 and through this space to wet the surface of object 6. Excess or residual water leaves the treatment zone defined by tube 8 through slits 34 formed in the tube. Since the gap between optical tip 5 and tube 8 is substantially smaller then the depth of space 17, there is a pressure build-up in space 17 which acts on holder 7 and traveling sleeve 12 attached thereto to raise the holder and sleeve, and thus raises light guide or tip 5 fixed in holder 7 from the surface of object 6. The tip remains raised, permitting water to hydrate and cool the zone of object 6 under the tip, until valve 21 is closed to terminate water flow. Similarly, pressurized air is applied to space 17 by turning on compressor 18, opening valve 22 and closing valves 21, 25, and 31. Pressurized air in space 17 also raises the tip in the same manner as the pressurized water, and also flows through the space between tip 5 and tube 8 to clean the surface of object 6, excess air, along with excess water and products of ablation and other dirt in the treatment zone flowing out of the zone through slits 34 in tube 8. Air pressurization of space 17 is ended by closing valve 22 and opening valves 25, 29, and 31, permitting the pressure in space 17 to be equalized to atmospheric pressure. This permits holder 7 and traveling tube 12, and thus tip 5 affixed thereto, to be moved downward by spring 35 until the tip is again in contact with the object 6. The distance that tip 5 is raised can vary with application, being approximately 100 to 150 µm for illustrative embodiments.

Figure 2:
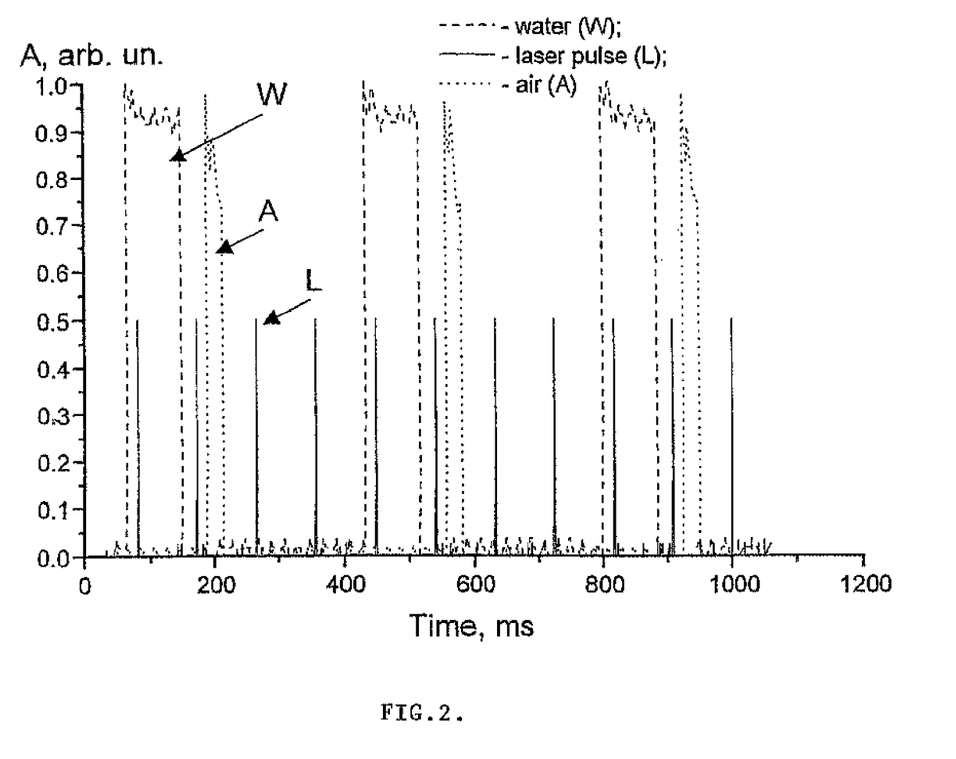
FIG. 2 is a diagram of an illustrative process sequence for practicing the invention.

All of the valves are electrically controlled by a suitable processor or other control mechanism to operate the laser radiation, water and air delivery in a desired sequence. One possible sequence is to operate the laser at a desired pulse repetition rate, for example 5-100 Hz., more preferable 10-30 Hz with water and air being applied in the intervals between each laser pulse, or between selected laser pulses, for example in the interval between every third pulse. Another option is for the application of water and the application of air to be between different ones of the laser pulses. Thus, water could be applied between every other laser pulse, with air being applied between the laser pulses where water is not applied. FIG. 2 illustrates still another option where the application of water W overlaps selected laser pulses L, with air A being applied in the interval between laser pulses after the interval during which the water is applied. In this case, the water pressure builds up slowly enough so that the tip does not rise off the surface of object 6 against the force of spring 35 until the overlapped laser pulse is over. The advantage of this embodiment is that water can also cool the object during and immediately after irradiation. Modeling data indicates that, where an Er laser is used, the thickness of the water film in the processing zone before irradiation by a laser pulse should be in the range 5-200 microns, and preferable 5-50 microns.

Figures 3, 3A:
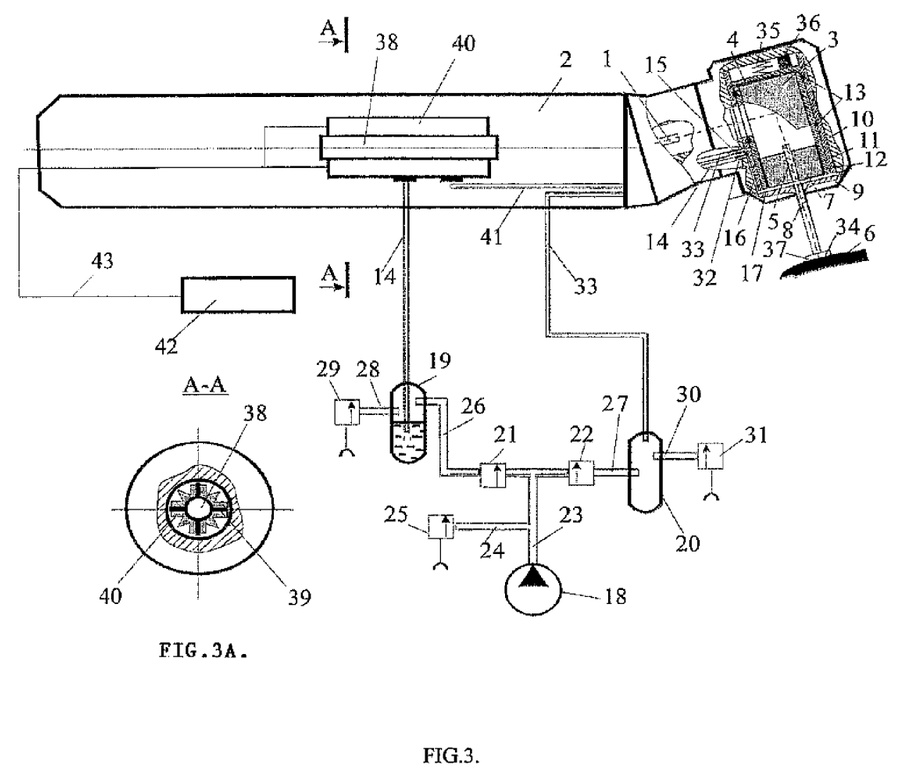
FIG. 3 is a partially cut-away illustration of a second embodiment of apparatus in accordance with the invention.
FIG. 3A is a sectional view taken along the line A-A in FIG. 3.

While for the embodiment of FIG. 1, tip 5 is raised by water pressure (hydraulic action) and air pressure (pneumatic action), this is not a limitation on the invention, and other suitable mechanisms may be utilized for the raising and lowering of the tip. For example, FIG. 3 shows a drive mechanism 37 positioned adjacent spring 35 which can be processor controlled to raise tip 5 as desired, the tip being lowered when mechanism 37 is deactivated under action of spring 35. Alternatively, mechanism 37 might be utilized to both raise and lower tip 5, with spring 35 no longer being required. Mechanism 37 may be a solenoid drive, electromagnetic drive, piezoelectric drive, other motor drive etc. and may for example transform electrical energy, magnetic field energy, mechanical energy or thermal energy into movement of the tip. The raising of tip 5 can also be effected by a blast effect from laser ablation on for example water on and in the object, a shock wave from the blast acting on the tip to raise it. On termination of the blast effect, spring 35 returns the tip to its lowered position in contact with object 6.

FIG. 3 also shows a reflector 36 mounted at the end of tube 8, the reflector being operative to increase the efficiency of the treatment device. The diameter of reflector 36 can be 0.1 mm to 4 mm in excess of the diameter of optical tip 5 for preferred embodiments. Reflector 36 functions differently depending on whether tip 5 is or is not in contact with object 6 during laser irradiation. If tip 5 is spaced from the surface of object 6 by some interval during irradiation, reflector 36 returns to the treatment zone products of laser ablation as fragments of solid particles. These particles further facilitate the ablation process in the manner generally described in the copending application, the subject matter of which application is incorporated herein in its entirety by reference. If optical tip 5 is in contact with the surface of object 6 during irradiation, ablation particles are directed to the area directly surrounding the treatment zone, generally facilitating the ablation process. In either event, shock waves resulting from the laser ablation are returned to the area of treatment and act on the object, for example dental enamel, to facilitate the ablation thereof. Slots 34 in reflector 36 perform the same functions as the slots 34 in tube 8, permitting the release of excess water and air, as well as products of ablation and other dirt to be removed from the treatment zone. Pressure or shock waves from ablation can also be used for raising the tip between pulses to facilitate cleaning products of ablation from the treatment zone. Spring 35, gas pressure, water pressure or other suitable mechanisms can be used to subsequently return the tip to contact with treatment zone 56.

Another embodiment of the invention includes a mechanism for moving or scanning the tip across or parallel to the treatment zone. The scanning mode can be 1D or 2D. This scanning can be combined with raising the tip perpendicular to treatment zone (3D scanning). Scanning of the tip can be done manually by a dentist or other operator. A feed back mechanism can be used to assist the manual scanning by showing when proper cleaning of products of ablation and any other dirt has occurred and/or where such cleaning is required. For example, an acoustic or optical signal may depend from detected ablation efficiency and/or material of ablation. If manual scanning it is not being performed properly to achieve desired results, the device, by sound or lighting, can inform the operator of the problem so that he can correct it. Automatic scanning control may also be possible in response to feedback signals.

Since the enhanced ablation efficiency resulting from practicing the teachings of the invention can result in a two to three fold and more improvement in ablation for a given laser pulse, practicing the teachings of the invention significantly lowers the energy requirements for the laser source used, and in particular, should permit the use of diode laser pumped solid state lasers as the radiation source. In the past, the energy needed for treatment has required too many diode lasers for such sources to be economically feasible. This may also permit the source to be small enough to fit in the treatment hand-piece, for example in the handle 2 thereof. The radiation source can, for example, be an Er:YAG crystal pumped by diode lasers with a wavelength of 960-980 nm. Other suitable active elements include, but are not limited to, Cr:ILF, Er:YSGG and other crystal doped with Cr, Tm and Ho with emitting wavelength 2.6-3.2 micron and an output energy of 1-1000 mJ with a repetition rate of 1-1000 Hz and a pulse width of $10(-9)-10(-2)$. The advantages of solid state lasers with diode pumping is that they are more efficient in converting electrical energy to optical energy and generally have a smaller size. Where less diodes are required, such source can also be less expensive.

Diode laser(s) may also be used alone as the radiation source. For example, a diode laser based on AlInGaAsSb/GaSb with separate confinement-heterostructure quantum well can be used to generate wavelengths in the band of peak absorption of water and hydroxiapatite, 2.6-3 microns. The diode laser(s) can be mounted in the hand piece and cooled by water, vaporized liquid or melted solid state (ie, ice).

In FIG. 3, the laser source is in the handle of the hand-piece. This arrangement is more reliable in that it eliminates the need for using accident-prone IR optical wave guides in an umbilical connecting the source to the hand-piece. However, this embodiment does require high energy electrical power cords in the umbilical which can be stiff, making the hand-piece more cumbersome to use. Referring to FIG. 3A, pumping of active rod 38 (for example, Er:YAG crystal) is accomplished by from two to ten diode bars 39. Active rod 38 and diode bars 39 are cooled by water from water tank 19, tube 14 leading through heat exchanger 40 for the laser source to tube 41 which connects to fitting 15 of housing 10. Diode bars 39 are connected to power supply 42 by electrical wires 43. The end surfaces of active rod 38 have dielectric coatings which function as mirrors for the laser cavity, the cavity lasing in standard fashion.

Figure 4:
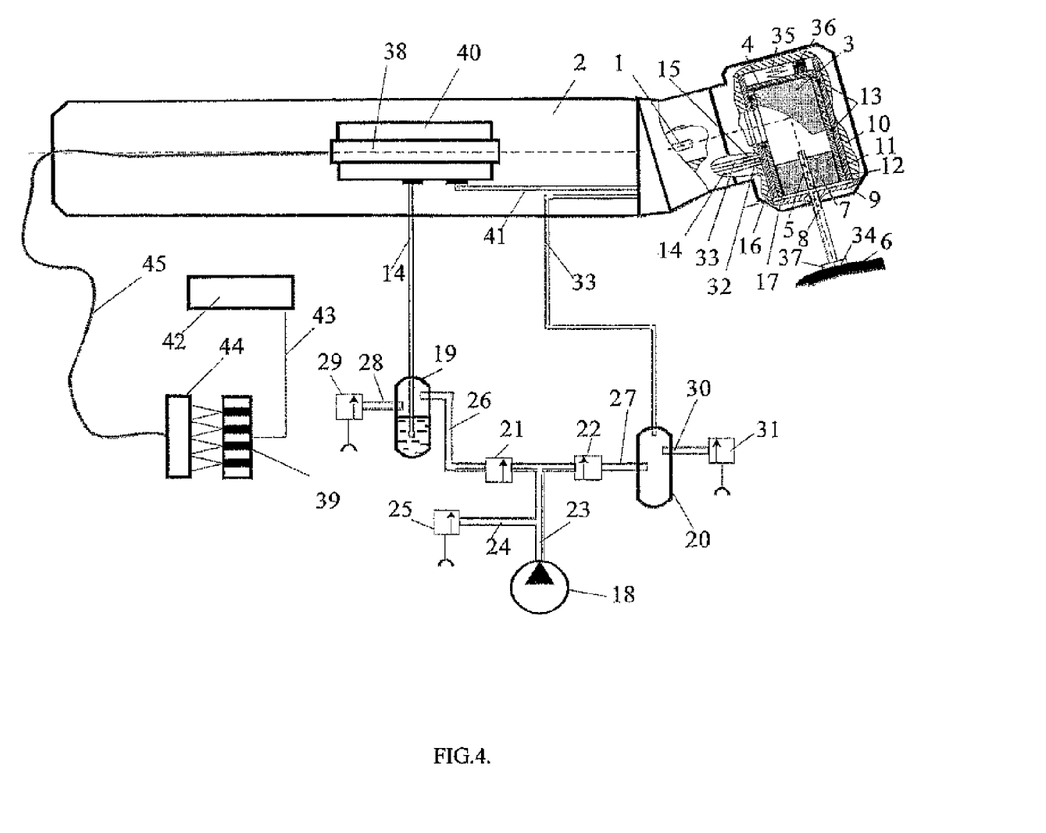
FIG. 4 is a partially cut-away illustration of a third embodiment of apparatus in accordance with the invention.
Figure 5:
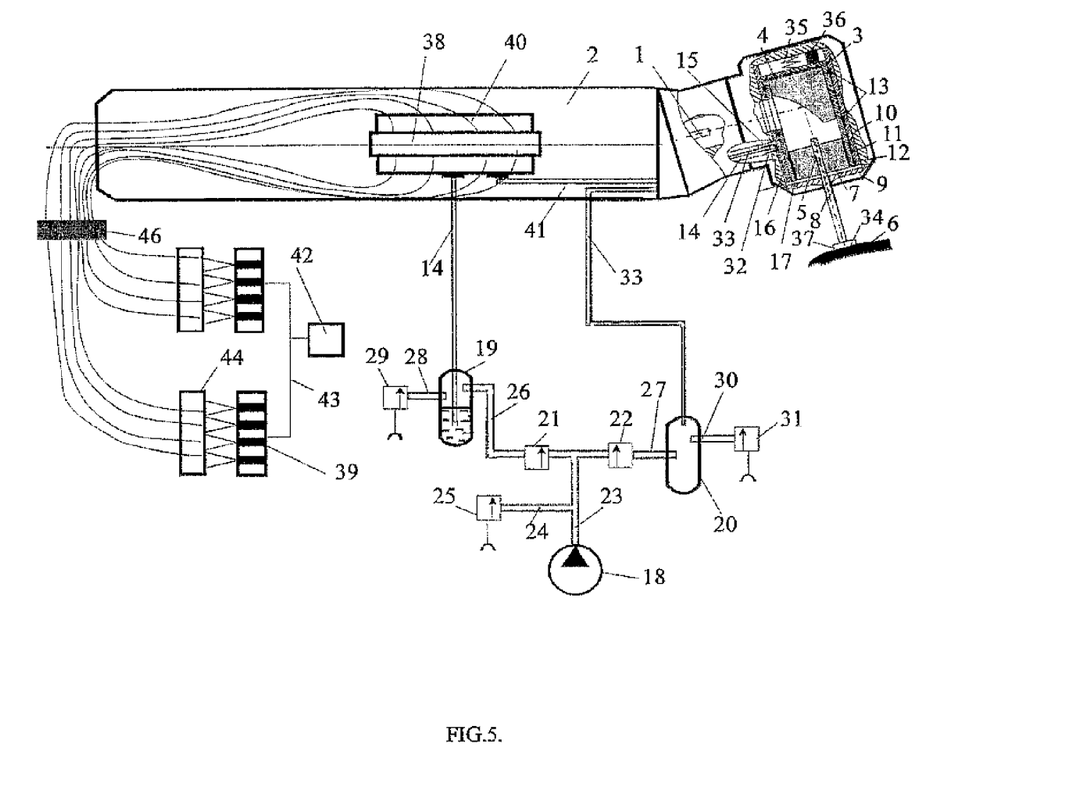
FIG. 5 is a partially cut-away illustration of a fourth embodiment of apparatus in accordance with the invention.

FIG. 4 shows the pumping of active rod 38 being done by diodes located outside the hand-piece. For this embodiment, radiation from a plurality of diode bars 39 pass through a suitable optical system 44 to enter an optical monofiber 45 connected to deliver the radiation to one end of the active rod. As shown in FIG. 5, pumping of active rod 38 can also be performed with optics which connect the outputs from the diodes 39 through suitable optical elements 44 and a plurality of optical fibers 45 to the walls of the active rod, the contact of the fibers with the walls permitting energy to enter the cavity for pumping. Element 46 is an optical connector.

Figures 6, 6A:
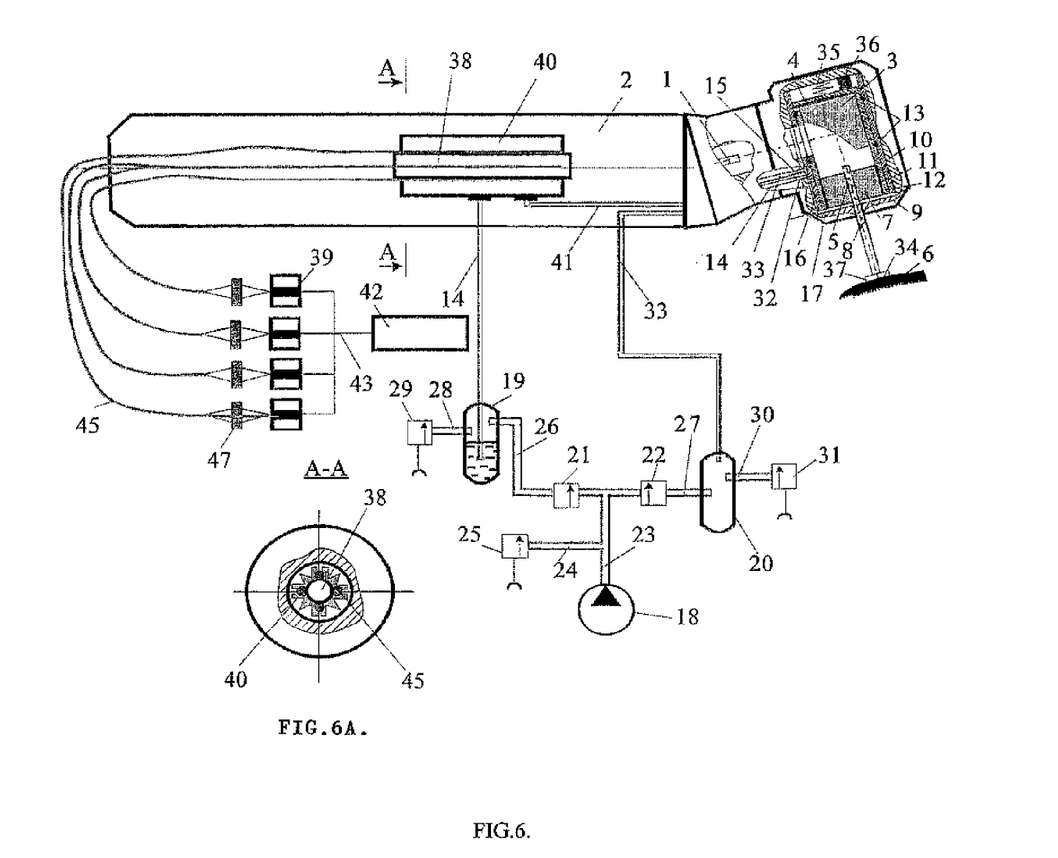
FIG. 6 is a partially cut-away illustration of a fifth embodiment of apparatus in accordance with the invention.
FIG. 6A is a sectional view taken along the line A-A in FIG. 6.

The pumping of active rod 38 can also be performed by use of several optical monofibers 45 connected to the active rod in a so called side pumping geometry as shown in FIG. 6. For this embodiment, radiation from each diode bar passes through a optical system 47 to the input of a monofiber 45. For the side pumping geometry, the fibers with removed cladding are in contact with the walls of the active rod along an extended length of the fiber and radiation from the fiber is coupled to the rod along this entire contact length. The refractive index of the crystal/rod is higher then the refractive index of the fiber 45.

In other embodiment active rod or slab 38 is mounted in non-doped cylinder 40 or between to non-doped plates with refractive index lower than the active rod and optically connected with the active rod or slab from a side surface thereof. This assembly has fiber laser geometry. Energy from the diode is coupled into a non-doped zone and from the non-doped zone, coupled into the active zone. This assembly can be made as a flexible fiber with doped core and non-doped cladding.

Figure 7:
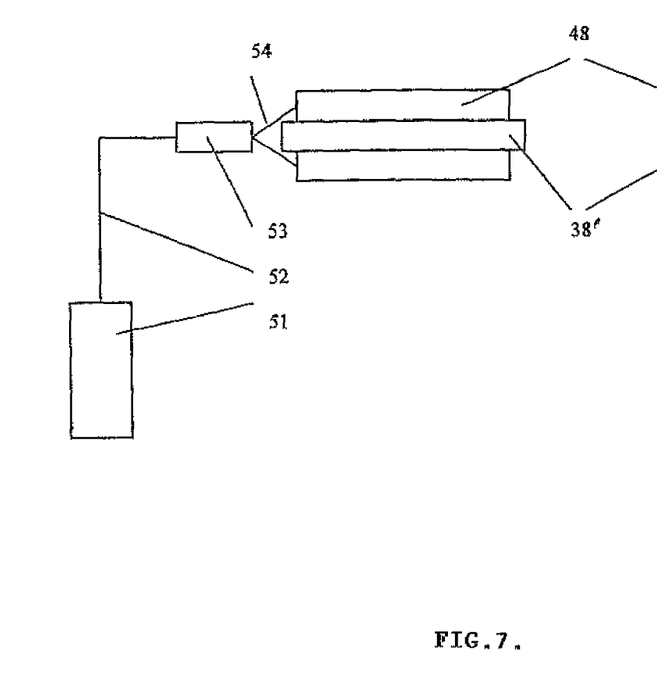
FIG. 7 is a schematic representation of a laser diode pumped solid state laser suitable for practicing the teachings of this invention.
Figure 7A:
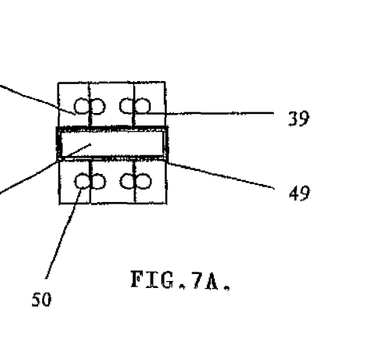
FIG. 7A is a sectional view taken along the line A-A in FIG. 7.

FIG. 7 shows a small, pumped solid-state laser which can be packaged into the hand-piece. Active element 38' (on FIG. 7 it is 46) is a slab or rod crystal doped by ions (for example Er). Active element 38' is pumped by diode bars 39' (not shown) mounted between electrodes/heat sinks 48. Electrodes/heat sinks 48 are thermally and electrically attached to bars 39' and thermally attached to active element 38'. The high reflective coating for diode bar wavelength 49 helps to couple diode energy into the active element. A high pressure compressed gas, for example R134A, from a can 51 is used for cooling active element 38', diodes 39' and electrodes/heat sinks 48. The low temperature liquid gas from can 51 is released into holes 50, a valve 53 being used to control the temperature of the cooled components to within a desired range. Tubes 52 and 54 are used for delivery of the gas to the laser assembly. High pressure gas or super cooled liquid, for example freon, nitrogen, or $CO_2$, can be used for cooling diode lasers and/or pumped solid state laser and/or or treatment tissue in all the various embodiments. Low pressure water with an evaporation temperature of 20-50 C. can also be used for same propose. In this case, the cooled side of the laser should be connected with a vacuum pump. In other embodiments, a melted or other phase change compound such as ice can be used to cool the diode laser and pumped solid state laser. Residual melted water can be used for cooling treated material/tissue.

A prototype of the invention described above was constructed and tested on laser removal/ablation of tooth enamel. During the experiments, a standard device of the general type shown in U.S. Pat. No. 5,257,956 was used with tip contact during irradiation and a sequence of irradiation, water application and pressurized air application generally as shown in FIG. 2. Human fresh extracted teeth were used. The laser source used was a pulsed Er:YAG laser operating at 2.94 μm and having a pulse width (FWHM) of (200±20) μs. Radiation energy at the optical tip output was about 210 mJ and the laser pulse repetition rate was 10 Hz. The diameter of the optical tip was 550 μm. The consumption of cooling water was (0.25±0.02) ml/min. The pressure formed by the compressor 18 was about 3 bar, this resulting in the raising of the tip from the enamel surface by approximately (120±15) μm. Enamel plates having a thickness of 1 mm were irradiated by a series of laser pulses having an energy density of (70±10) $J/cm^2$, irradiation stopping when through ablation of the plate occurred. Enamel removal velocity was calculated as a ratio of plate thickness to the number of laser pulses used to achieve through ablation. It was found that, while enamel removal velocity for a standard device was (21±3) μm/pulse, enamel laser removal velocity utilizing the teachings of this invention was (55±5) μm/pulse. Thus, the device utilizing the teachings of this invention was about 2.5 faster in treatment then the standard one.

While for the illustrative embodiments shown, only tip 5 is raised to facilitate hydration and cleaning of the object surface under the tip, this is not a limitation on the invention, and the objective of raising the tip could also be accomplished by having tube 8 and tip 5 raised together, by raising housing 10 or in other suitable ways. Similarly, while a mechanical spring 35 has been show as the return mechanism for the illustrative embodiments, other suitable elastic components might be utilized to perform this function, for example an air spring or an elastomer. Further, while the invention has been used to treat tooth enamel for preferred embodiments, the invention could also be used to treat other hard materials such as bone tissue, metals, diamond, sapphire, etc. Other variations in the details of construction are also within the contemplation of the invention. Thus, while the invention has been particularly shown and described above with reference to preferred embodiments, the forgoing and other changes in form and detail may be made therein by one skilled in the art while still remaining within the spirit and scope of the invention, which is to be defined only by the following claims.

The invention claimed is:

1. A dental laser ablation system comprising a hand piece comprising a scanning tip for delivering laser radiation used for ablation of hard tissue to a treatment zone, the scanning tip coupled to a control mechanism automatically controlling a scanning mode of the scanning tip, wherein the laser radiation is generated by a diode laser, diode pumped solid state laser, or diode pumped fiber laser and wherein a wavelength of the laser radiation is selected from a range from 2.5 μm to 3.2 μm, wherein energy of the laser radiation is selected from a range from 1 to 1000 mJ, wherein a pulse repetition rate of the laser radiation is selected from a range from 1 to 2000 Hz, and wherein a pulse duration of the laser radiation is selected from a range from $10^{-9}$ to $10^{-2}$ sec.

2. The dental laser system of claim 1, wherein the handpiece comprises a laser head of the laser for generating the laser radiation.

3. The dental laser system of claim 1, further comprising a umbilical housing a fiber laser and wherein the umbilical is connected to the source housed in the connector.

4. The dental laser system of claim 1, wherein the laser radiation is generated by the diode pumped solid state laser.

5. The dental laser system according to claim 1, wherein the diode laser is housed in the connector or a housing and wherein the pump source delivers the laser radiation via a fiber.

6. The dental laser system according to claim 1, wherein the diode pumped solid state laser is simultaneously end pumped and side pumped.

7. The dental laser system according to claim 1, wherein the scanning tip can be moved away from the treatment zone due to a blast effect of laser ablation.

8. The dental laser of claim 1, wherein the scanning tip is capable of one-dimensional motion.

9. The dental laser of claim 1, wherein the scanning tip is capable of two-dimensional motion.

10. The dental laser of claim 1, wherein the scanning tip is capable of three-dimensional motion.

11. The dental laser system according to claim 1, wherein the scanning tip can be raised and lowered by a mechanism transforming electrical energy, magnetic energy, mechanical energy, thermal energy into a movement of the scanning tip.

* * * * *